(12) United States Patent
Chen

(10) Patent No.: US 7,632,809 B2
(45) Date of Patent: Dec. 15, 2009

(54) MULTIMERIC LIGANDS WITH ENHANCED STABILITY

(75) Inventor: Wen Yuan Chen, Clemson, SC (US)

(73) Assignee: Oncolix, Inc., Houston, TX (US)

( * ) Notice: Subject to any disclaimer, the term of this patent is extended or adjusted under 35 U.S.C. 154(b) by 374 days.

(21) Appl. No.: 10/419,976

(22) Filed: Apr. 22, 2003

(65) Prior Publication Data

US 2004/0033948 A1   Feb. 19, 2004

Related U.S. Application Data

(60) Provisional application No. 60/374,137, filed on Apr. 22, 2002.

(51) Int. Cl.
*A61K 38/27* (2006.01)
*A61K 38/18* (2006.01)
*C07K 14/61* (2006.01)
*C07K 14/475* (2006.01)
*C12P 21/06* (2006.01)

(52) U.S. Cl. .......................... 514/12; 530/324; 435/69.1
(58) Field of Classification Search .................... None
See application file for complete search history.

(56) References Cited

U.S. PATENT DOCUMENTS

| | | | |
|---|---|---|---|
| 5,350,836 A | 9/1994 | Kopchick et al. | |
| 5,681,809 A | 10/1997 | Kopchick et al. | |
| 5,958,879 A | 9/1999 | Kopchick et al. | |
| 6,787,336 B1 | 9/2004 | Kopchick et al. | |
| 6,875,741 B2* | 4/2005 | Pillutla et al. | 514/12 |
| 2006/0252697 A1* | 11/2006 | Blume et al. | 514/13 |

OTHER PUBLICATIONS

Goffin et al., Journal of Biological Chemistry, 271(28):16573-16579, 1996.*
Chawla, R.K., et al., "Structural Variants of Human Growth Hormone", Ann. Rev. Med. (1983), vol. 34, pp. 519-547.
Edwards, C.K., et al., "A Newly Defined Property of Somatotropin: Priming of Macrophages for Production of Superoxide Anion", Science, (1988) vol. 239, pp. 769-771.
Venkatachalam, M.A., et al., Energy Thresholds that Determine Membrane Integrity and Injury in a Renal Epithelial Cell Line (LLC-$PK_1$); The Journal of Clinical Investigation (1988) vol. 81, No. 3, pp. 745-758.
Logan, J., et al., "Adenovirus Tripartite Leader Sequence Enhances Translation of mRNAs Late After Infection", Molecular Endocrinology, (1995) vol. 9, No. 12, pp. 3655-3659.
Altschul, S.F., et al., "Basic Local Alignment Search Tool", J. Mol. Biol. (1990) vol. 215, pp. 403-410.
Gish, W., et al., "Identification of Protein Coding Regions by Database Similarity Search", Nature Genetics, (1993), vol. 3, pp. 266-272.

Madden, T.L., et al., "Applications of Network Blast Server", Methods in Enzymology, (1996), vol. 266, pp. 131-141.
Altschul, S.F., et al., "Gapped Blast and PSI-Blast: A New Generation of Protein Database Search Programs", Nucleic Acids Research (1997) vol. 25, No. 17, pp. 3389-3402.
Zhang, J., et al., "PowerBlast: A New Network Blast Application for Interactive or Automated Sequence Analysis and Annotation", Genome Research (1997) vol. 7, pp. 649-656.
Zhang et al., "A Novel Design of Targeted Endocrine and Cytokine Therapy for Breast Cancer," Vol. 8, 1196-1205, Apr. 2002.
Qiu, H. et al.: "Homodimerization Restores Biological Activity to an Inactive Erythropoietin Mutant", *The Journal of Biological Chemistry*, The American Society for Biochemistry and Molecular Biology, Inc. (May 1998), pp. 11173-11176, vol. 273, No. 18, U.S. (XP002453390).
Langenheim, J. F. et al.: "Two Wrongs Can Make a Right: Dimers of Prolactin and Growth Hormone Receptor Antagonists Behave as Agonists", *Molecular Endocrinology*, The Endocrine Society (Mar. 2006), pp. 661-674, vol. 20, No. 3, U.S. (XP009089441).
Goffin, V. et al.: "Development of New Prolacting Analogs Acting as Pure Prolactin Receptor Anatgonists", *Pituitary*, Kluwer Academic Publishers (Jun. 2003), pp. 89-95, vol. 6, No. 2, U.S. (XP019214353).
Chen, N.Y. et al.: "In vivo studies of the anti-tumor effects of a human prolactin antagonist, hPRL-G129R", *International Journal of Oncology*, Editorial Academy Of The International Journal Of Oncology (Jan. 2002), pp. 813-818, vol. 20, U.S. (XP002993163).
Chen, W. Y. et al.: "a Human Prolactin Antagonist, hPRL-G129R, Inhibits Breast Cancer Cell Proliferation through Induction of Apoptosis[1]", *Clinical Cancer Research*, The American Association For Cancer Research (Nov. 1999), pp. 3583-3593, vol. 5, No. 11, U.S. (XP002276493).
Cataldo, L. et al.: "Inhibition of oncogene STAT3 phosphorylation by a prolactin antagonist, hPRL-G129R, in T-47D human breast cancer cells", *International Journal of Oncology*, Oncology Research Institute (Dec. 2000), pp. 1179-1185, vol. 17, No. 6, U.S. (XP009089739).
Sytkowski, A. J. et al.: "An Erythropoietin Fusion Protein Comprised of Identical Repeating Domains Exhibits Enhanced Biological Properties", *The Journal of Biological Chemistry*, American Society of Biolochemical Biologists (Aug. 1999), pp. 24773-24778, vol. 274, No. 35, U.S. (XP002354910).
Dalle Bruno et al.: "Dimeric erythropoietin fusion protein with enhanced erythropoietic activity in vitro and in vivo", *Blood*, The American Society of Hematology (Jun. 2001), pp. 3776-3782, vol. 97, No. 12, U.S. (XP002453391).

* cited by examiner

*Primary Examiner*—Marianne P Allen
(74) *Attorney, Agent, or Firm*—Howrey LLP

(57) ABSTRACT

The present invention provides compositions and methods for making multimeric proteins to increase stability over their monomer. For example, more stable growth hormone and prolactin receptor agonists are provided.

11 Claims, 3 Drawing Sheets

Activation of STAT5 Phosphorylation

Competitive Inhibition of STAT5 Phosphorylation

SEQUENCE LISTING

<160> NUMBER OF SEQ ID NOS: 32

<210> SEQ ID NO 1
<211> LENGTH: 22
<212> TYPE: PRT
<213> ORGANISM: Homo sapiens
<220> FEATURE:
<221> NAME/KEY: misc_feature
<222> LOCATION: (18)..(18)
<223> OTHER INFORMATION: Xaa can be any naturally occurring amino acid

<400> SEQUENCE: 1

Ile Glu Glu Gln Thr Lys Arg Leu Leu Arg Gly Met Glu Leu Ile Val
1               5                   10                  15

Ser Xaa Gln Val His Pro
            20

<210> SEQ ID NO 2
<211> LENGTH: 22
<212> TYPE: PRT
<213> ORGANISM: Rattus sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 2

Ile Glu Glu Gln Asn Lys Arg Leu Leu Glu Gly Ile Glu Lys Ile Ile
1               5                   10                  15

Gly Xaa Gln Ala Tyr Pro
            20

<210> SEQ ID NO 3
<211> LENGTH: 22
<212> TYPE: PRT
<213> ORGANISM: Mus sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 3

Ile Glu Glu Gln Asn Lys Gln Leu Leu Glu Gly Val Glu Lys Ile Ile
1               5                   10                  15

Ser Xaa Gln Ala Tyr Pro
            20

<210> SEQ ID NO 4
<211> LENGTH: 22
<212> TYPE: PRT
<213> ORGANISM: Hamster sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 4

Ile Gly Glu Gln Asn Lys Arg Leu Leu Glu Gly Ile Glu Lys Ile Leu
1               5                   10                  15

Gly Xaa Gln Ala Tyr Pro
            20

<210> SEQ ID NO 5
<211> LENGTH: 22

```
<212> TYPE: PRT
<213> ORGANISM: Balaena glacialis
<220> FEATURE:
<221> NAME/KEY: misc_feature
<222> LOCATION: (18)..(18)
<223> OTHER INFORMATION: Xaa can be any naturally occurring amino acid

<400> SEQUENCE: 5

Glu Glu Glu Glu Asn Lys Arg Leu Leu Glu Gly Met Glu Lys Ile Val
1               5                   10                  15

Gly Xaa Gln Val His Pro
            20

<210> SEQ ID NO 6
<211> LENGTH: 22
<212> TYPE: PRT
<213> ORGANISM: Mustela sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 6

Ile Glu Glu Glu Asn Arg Arg Leu Leu Glu Gly Met Glu Lys Ile Val
1               5                   10                  15

Gly Xaa Gln Val His Pro
            20

<210> SEQ ID NO 7
<211> LENGTH: 22
<212> TYPE: PRT
<213> ORGANISM: Bos sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 7

Ile Glu Glu Gln Asn Lys Arg Leu Ile Glu Gly Met Glu Met Ile Phe
1               5                   10                  15

Gly Xaa Gln Val Ile Pro
            20

<210> SEQ ID NO 8
<211> LENGTH: 22
<212> TYPE: PRT
<213> ORGANISM: Ovis sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 8

Glu Glu Glu Glu Asn Lys Arg Leu Leu Glu Gly Met Glu Asn Ile Phe
1               5                   10                  15

Gly Xaa Gln Val Ile Pro
            20

<210> SEQ ID NO 9
<211> LENGTH: 22
<212> TYPE: PRT
<213> ORGANISM: Sus sp.
<220> FEATURE:
<221> NAME/KEY: misc_feature
<222> LOCATION: (18)..(18)
<223> OTHER INFORMATION: Xaa can be any naturally occurring amino acid
```

```
<400> SEQUENCE: 9

Ile Glu Glu Gln Asn Lys Arg Leu Leu Glu Gly Met Glu Lys Ile Val
1               5                   10                  15

Gly Xaa Gln Val His Pro
            20

<210> SEQ ID NO 10
<211> LENGTH: 22
<212> TYPE: PRT
<213> ORGANISM: Camelus sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 10

Ile Glu Glu Gln Asn Lys Arg Leu Leu Glu Gly Met Glu Lys Ile Val
1               5                   10                  15

Gly Xaa Gln Val His Pro
            20

<210> SEQ ID NO 11
<211> LENGTH: 22
<212> TYPE: PRT
<213> ORGANISM: Equus sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 11

Glu Ile Glu Gln Asn Arg Arg Leu Leu Glu Gly Met Glu Lys Ile Val
1               5                   10                  15

Gly Xaa Gln Val Gln Pro
            20

<210> SEQ ID NO 12
<211> LENGTH: 22
<212> TYPE: PRT
<213> ORGANISM: Elephant
<220> FEATURE:
<221> NAME/KEY: misc_feature
<222> LOCATION: (18)..(18)
<223> OTHER INFORMATION: Xaa can be any naturally occurring amino acid

<400> SEQUENCE: 12

Val Lys Glu Glu Asn Gln Arg Leu Leu Glu Gly Ile Glu Lys Ile Val
1               5                   10                  15

Asp Xaa Gln Val His Pro
            20

<210> SEQ ID NO 13
<211> LENGTH: 22
<212> TYPE: PRT
<213> ORGANISM: Ancestral Mammal
<220> FEATURE:
<221> NAME/KEY: misc_feature
<222> LOCATION: (18)..(18)
<223> OTHER INFORMATION: Xaa can be any naturally occurring amino acid

<400> SEQUENCE: 13

Ile Glu Glu Glu Asn Lys Arg Leu Leu Glu Gly Met Glu Lys Ile Val
1               5                   10                  15

Gly Xaa Gln Val His Pro
            20
```

<210> SEQ ID NO 14
<211> LENGTH: 22
<212> TYPE: PRT
<213> ORGANISM: Gallus sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 14

Ile Glu Glu Gln Asn Lys Arg Leu Leu Glu Gly Met Glu Lys Ile Val
1               5                   10                  15

Gly Xaa Arg Val His Ser
            20

<210> SEQ ID NO 15
<211> LENGTH: 22
<212> TYPE: PRT
<213> ORGANISM: Meleagris Sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 15

Ile Glu Glu Gln Asp Lys Arg Leu Leu Glu Gly Met Glu Lys Ile Val
1               5                   10                  15

Gly Xaa Arg Ile His Ser
            20

<210> SEQ ID NO 16
<211> LENGTH: 22
<212> TYPE: PRT
<213> ORGANISM: Sea Turtle
<220> FEATURE:
<221> NAME/KEY: misc_feature
<222> LOCATION: (18)..(18)
<223> OTHER INFORMATION: Xaa can be any naturally occurring amino acid

<400> SEQUENCE: 16

Ile Glu Glu Gln Asn Lys Arg Leu Leu Glu Gly Met Glu Lys Ile Val
1               5                   10                  15

Gly Xaa Gln Val His Pro
            20

<210> SEQ ID NO 17
<211> LENGTH: 22
<212> TYPE: PRT
<213> ORGANISM: Crocodile Sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 17

Ile Glu Glu Gln Asn Lys Arg Leu Leu Glu Gly Met Glu Lys Ile Ile
1               5                   10                  15

Gly Xaa Arg Val Gln Pro
            20

<210> SEQ ID NO 18
<211> LENGTH: 22
<212> TYPE: PRT
<213> ORGANISM: Alligator Sp.
<220> FEATURE:

```
<221> NAME/KEY: misc_feature
<222> LOCATION: (18)..(18)
<223> OTHER INFORMATION: Xaa can be any naturally occurring amino acid

<400> SEQUENCE: 18

Ile Glu Glu Gln Asn Lys Arg Leu Leu Glu Gly Met Glu Lys Val Ile
1               5                   10                  15

Gly Xaa Arg Val Gln Pro
            20

<210> SEQ ID NO 19
<211> LENGTH: 22
<212> TYPE: PRT
<213> ORGANISM: Ancestral Amniote Sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 19

Ile Glu Glu Gln Asn Lys Arg Leu Leu Glu Gly Met Glu Lys Ile Val
1               5                   10                  15

Gly Xaa Gln Val His Pro
            20

<210> SEQ ID NO 20
<211> LENGTH: 22
<212> TYPE: PRT
<213> ORGANISM: Xenopus sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 20

Val Glu Glu Gln Asn Lys Arg Leu Leu Glu Gly Met Glu Lys Ile Val
1               5                   10                  15

Gly Xaa Arg Ile His Pro
            20

<210> SEQ ID NO 21
<211> LENGTH: 22
<212> TYPE: PRT
<213> ORGANISM: Rana sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 21

Val Glu Glu Gln Thr Lys Arg Leu Leu Glu Gly Met Glu Arg Ile Ile
1               5                   10                  15

Gly Xaa Arg Ile Gln Pro
            20

<210> SEQ ID NO 22
<211> LENGTH: 22
<212> TYPE: PRT
<213> ORGANISM: Lungfish Sp.
<220> FEATURE:
<221> NAME/KEY: misc_feature
<222> LOCATION: (18)..(18)
<223> OTHER INFORMATION: Xaa can be any naturally occurring amino acid

<400> SEQUENCE: 22

Val Glu Asp Gln Thr Lys Gln Leu Ile Glu Gly Met Glu Lys Ile Leu
```

```
                1               5                   10                  15

Ser Xaa Arg Met His Pro
            20

<210> SEQ ID NO 23
<211> LENGTH: 22
<212> TYPE: PRT
<213> ORGANISM: Tilapia Sp.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 23

Met Gln Gln Tyr Ser Lys Ser Leu Lys Asp Gly Leu Asp Xaa Val Leu
1               5                   10                  15

Ser Ser Lys Met Gly Ser
            20

<210> SEQ ID NO 24
<211> LENGTH: 22
<212> TYPE: PRT
<213> ORGANISM: Tilapia Sp.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 24

Met Gln Glu His Ser Lys Asp Leu Lys Asp Gly Leu Asp Xaa Ile Leu
1               5                   10                  15

Ser Ser Lys Met Gly Pro
            20

<210> SEQ ID NO 25
<211> LENGTH: 22
<212> TYPE: PRT
<213> ORGANISM: Cyprinus Carpio
<220> FEATURE:
<221> NAME/KEY: misc_feature
<222> LOCATION: (17)..(17)
<223> OTHER INFORMATION: Xaa can be any naturally occurring amino acid

<400> SEQUENCE: 25

Leu Gln Glu Asn Ile Asn Ser Leu Gly Ala Gly Leu Glu His Val Phe
1               5                   10                  15

Xaa Asn Lys Met Asp Ser
            20

<210> SEQ ID NO 26
<211> LENGTH: 22
<212> TYPE: PRT
<213> ORGANISM: Bighead Carp
<220> FEATURE:
<221> NAME/KEY: misc_feature
<222> LOCATION: (17)..(17)
<223> OTHER INFORMATION: Xaa can be any naturally occurring amino acid

<400> SEQUENCE: 26

Leu Gln Asp Asn Ile Asn Ser Leu Gly Ala Gly Leu Glu Arg Val Val
1               5                   10                  15

Xaa His Lys Met Gly Ser
            20

<210> SEQ ID NO 27
```

```
<211> LENGTH: 22
<212> TYPE: PRT
<213> ORGANISM: Silver Carp
<220> FEATURE:
<221> NAME/KEY: misc_feature
<222> LOCATION: (17)..(17)
<223> OTHER INFORMATION: Xaa can be any naturally occurring amino acid

<400> SEQUENCE: 27

Leu Gln Asp Asn Ile Asn Ser Leu Val Pro Gly Leu Glu His Val Val
1               5                   10                  15

Xaa His Lys Met Gly Ser
            20

<210> SEQ ID NO 28
<211> LENGTH: 22
<212> TYPE: PRT
<213> ORGANISM: Chun Salmon
<220> FEATURE:
<221> NAME/KEY: misc_feature
<222> LOCATION: (14)..(14)
<223> OTHER INFORMATION: Xaa can be any naturally occurring amino acid

<400> SEQUENCE: 28

Leu Gln Asp Tyr Ser Lys Ser Leu Gly Asp Gly Leu Asp Xaa Ile Met
1               5                   10                  15

Val Asn Lys Met Gly Pro
            20

<210> SEQ ID NO 29
<211> LENGTH: 22
<212> TYPE: PRT
<213> ORGANISM: Chinook Salmon
<220> FEATURE:
<221> NAME/KEY: misc_feature
<222> LOCATION: (14)..(14)
<223> OTHER INFORMATION: Xaa can be any naturally occurring amino acid

<400> SEQUENCE: 29

Leu Gln Asp Tyr Ser Lys Ser Leu Gly Asp Gly Leu Asp Xaa Ile Met
1               5                   10                  15

Val Asn Lys Met Gly Pro
            20

<210> SEQ ID NO 30
<211> LENGTH: 22
<212> TYPE: PRT
<213> ORGANISM: Trout Sp.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 30

Leu Gln Asp Tyr Ser Lys Ser Leu Gly Asp Gly Leu Asp Xaa Ile Met
1               5                   10                  15

Val Asn Lys Met Gly Pro
            20

<210> SEQ ID NO 31
<211> LENGTH: 22
<212> TYPE: PRT
<213> ORGANISM: Homo sapiens

<400> SEQUENCE: 31

Tyr Tyr Asp Leu Leu Lys Asp Leu Glu Glu Gly Ile Gln Thr Leu Met
```

```
                        -continued
1               5                   10                  15

Arg Glu Leu Glu Asp Gly
            20

<210> SEQ ID NO 32
<211> LENGTH: 22
<212> TYPE: PRT
<213> ORGANISM: Unknown
<220> FEATURE:
<223> OTHER INFORMATION: Bovine sequence

<400> SEQUENCE: 32

Val Tyr Glu Lys Leu Lys Asp Leu Glu Glu Gly Ile Leu Ala Leu Met
1               5                   10                  15

Arg Glu Leu Glu Asp Gly
            20
```

MULTIMERIC LIGANDS WITH ENHANCED STABILITY

STATEMENT OF SUPPORT

Supported in part by the Endowment Fund of the Greenville Hospital System and Grants (DAMD17-99-1-9129, DAMD17-01-1-0207, NIH/NCI 1R21CA87093).

FIELD OF THE INVENTION

The present invention relates generally to compositions and methods of preparing multimeric ligands with enhanced stability.

BACKGROUND OF THE INVENTION

Prolactin (PRL) is a neuroendocrine polypeptide hormone primarily produced by the lactotrophs of the anterior pituitary gland in all vertebrates. Human prolactin (hPRL) is a 23 kDa protein that binds the prolactin receptor.

Human growth hormone (hGH) differs from human prolactin at about 25% of its residues. Wallis et al., supra. hGH participates in much of the regulation of normal human growth and development. This 22,000 dalton pituitary hormone regulates a multitude of biological effects including linear growth (somatogenesis), lactation, activation of macrophages, insulin-like effects and diabetagenic effects among others. See Chawla, R. K. (1983) Ann. Rev. Med. 34, 519; Edwards, C. K., et al. (1988) Science 239, 769; Thorner, M. O., et al. (1988) J. Clin. Invest. 81, 745.

In adults, the consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced. Administration of exogenous growth hormone has been shown to reverse many of the metabolic changes. Additional benefits of therapy have included reduction in LDL cholesterol and improved psychological well-being.

To increase levels of growth hormone, exogenous growth hormone may be administered. Historically, the source of growth hormone had been the pituitary glands of cadavers. Extraction of growth hormone from this source, however, resulted in an expensive product that carried the risk of disease. Accordingly, this product has largely been displaced by recombinant growth hormone, thereby alleviating a risk of disease transmission, the product is still very expensive.

Accordingly, there is a need in the art for a more stable, longer acting growth hormone, that is equally or more effective than the growth hormone currently available in the art. A growth hormone with a longer serum half-life would off-set the frequency of growth hormone administration and therefore the expense associated with the growth hormone used in current treatment regimens.

Similarly, enhancing the stability of other ligands would also result in lower cost associated with exogenous hormone treatment.

SUMMARY OF THE INVENTION

It is an object of the invention to provide a multimeric ligand that has a prolonged serum half-life. The proteins of the present invention exhibit enhanced stability compared to its monomer.

Provided herein is a receptor binding multimer, such as a receptor antagonist multimer or a receptor agonist multimer, wherein the receptor binding multimer acts as a receptor agonist. In a preferred embodiment, the receptor binding multimer is a dimer. Also preferred, the receptor binding multimer is a receptor antagonist homodimer or a receptor agonist homodimer. It is also preferred that the receptor antagonist monomers of the receptor antagonist homodimer are selected from the group consisting of a prolactin receptor antagonist monomer and a growth hormone receptor antagonist monomer. However, it is also receptor antagonist multimer comprises at least one growth hormone receptor antagonist monomer and at least one prolactin antagonist monomer. It is also preferred that the receptor agonist monomers of the receptor agonist homodimer are selected from the group consisting of a prolactin receptor agonist monomer and a growth hormone receptor agonist monomer. However, it is also considered that the receptor agonist multimer comprises at least one growth hormone receptor agonist monomer and at least one a prolactin agonist monomer.

Generally, the prolactin receptor antagonist monomers may comprise an amino acid substitution at a position corresponding to 129 in hPRL, such as a hPRL-R129G monomer. Also, the growth hormone receptor antagonist monomers may comprise an amino acid substitution at a position corresponding to 120 in hGH, such as a hGH-R120G monomer. Examples of a prolactin receptor agonist monomer and a growth hormone receptor agonist monomer include a wild-type hPRL monomer and a wild-type hGH monomer, respectively.

Also contemplated in the present invention is a receptor binding multimer that comprises a receptor antagonist monomer and a receptor agonist monomer. For example, a receptor binding multimer as described herein includes a hPRL-hPRL-G129R heterodimer as well as a hGH-hGH-G120R heterodimer. Similarly, a hPRL-hGH heterodimer is also contemplated.

Also provided herein is a pharmaceutical composition comprising a therapeutically useful amount of any of the multimers described herein and a pharmaceutically suitable excipient.

Contemplated in the present invention is a method for increasing growth hormone cell signaling or prolactin cell signaling, comprising administering to a patient an effective amount of any of the receptor binding multimers described herein. In a preferred embodiment, the growth hormone receptor binding multimer is a growth hormone antagonist receptor homodimer or a growth hormone receptor agonist homodimer. Similarly, it is also preferred that the prolactin receptor binding multimer is a prolactin receptor agonist homodimer or a prolactin receptor antagonist homodimer. Also preferred are prolactin receptor binding multimers that comprise at least one prolactin receptor antagonist monomer and at least one prolactin receptor agonist monomer, as well as growth hormone receptor binding multimers that comprise at least one growth hormone receptor antagonist monomer and at least one growth hormone receptor agonist monomer.

Also described herein is a method of treating a disease, disorder, or condition comprising administering to a patient an effective amount of a protein comprising a receptor binding multimer, including a receptor antagonist multimer or a receptor agonist multimer. In a preferred embodiment, the receptor binding multimer is a dimer. Also preferred, the receptor binding multimer is a receptor antagonist homodimer or a receptor agonist homodimer. It is also preferred that the receptor antagonist monomers of the receptor antagonist homodimer are prolactin receptor antagonist monomers or growth hormone receptor antagonist monomers. However, it is also considered that the receptor antagonist monomers of the receptor antagonist multimer comprise a growth hormone receptor antagonist monomer and a prolactin antagonist monomer. It is also preferred that the receptor agonist monomers of the receptor agonist homodimer are prolactin receptor agonist monomers or growth hormone receptor agonist monomers. Alternatively, the receptor agonist monomers of the receptor agonist multimer may comprise a growth hormone receptor agonist monomer and a prolactin agonist monomer.

The multimers of the present invention can be used to treat various diseases, disorders or conditions, depending on the multimer administered. Exemplary diseases, disorders or conditions include immunodepression, supplementing ovarian stimulation for in vitro fertilization, restoring normal sperm in infertile men, dwarfism, osteoporosis, congestive heart failure, frailty associated with aging, obesity, accelerating bone fracture repair, attenuating protein catabolic response after a major operation, reducing cachexia and protein loss due to chronic illness, accelerating wound healing, accelerating recovery of burn patients, accelerating recovery of patients having undergone major surgery, improving muscle strength, mobility, maintenance of skin thickness, maintenance of metabolic homeostasis and maintenance of renal homeostasis It is also considered that the method of treating a disease, disorder or condition comprises administering to a patient an effective amount of a receptor binding multimer that comprises a receptor antagonist monomer and a receptor agonist monomer.

In another embodiment of the present invention is a method of making a receptor agonist comprising designing a cDNA encoding a receptor antagonist multimer which links the C terminus of the first receptor antagonist monomer with the N terminus of the second receptor antagonist monomer In a related vein, a method of making a receptor agonist comprising designing a cDNA encoding a receptor agonist multimer which links the C terminus of the first receptor agonist monomer with the N terminus of the second receptor agonist monomer is also described. Preferably, the first and second receptor agonist monomers are selected from the group consisting of a prolactin receptor agonist monomer and a growth hormone receptor agonist monomer. Also preferred, the first and second receptor antagonist monomers are selected from the group consisting of a prolactin receptor antagonist monomer and a growth hormone receptor antagonist monomer. Similarly, method of making a receptor agonist comprising designing a cDNA encoding a receptor binding multimer which links the C terminus of the first receptor agonist monomer with the N terminus of the second receptor antagonist monomer, and the reverse, is also considered.

A DNA construct comprising the nucleotide sequence of the receptor antagonist multimer or a receptor agonist multimer is also contemplated in the present invention. In a related vein, a DNA construct comprising the nucleotide sequence of the receptor binding multimer, wherein said receptor binding multimer comprises a receptor agonist monomer and a receptor antagonist monomer is also considered.

Finally, a method of increasing protein stability comprising making a receptor binding multimer, such as a receptor agonist multimer or a receptor antagonist multimer, is described. Preferably the receptor agonist multimer comprises a receptor agonist monomer that is a prolactin receptor agonist monomer or a growth hormone receptor agonist monomer. However, the receptor antagonist multimer may comprise a prolactin receptor antagonist monomer and a growth hormone receptor antagonist monomer.

DETAILED DESCRIPTION OF THE PREFERRED EMBODIMENTS

Figure 1:
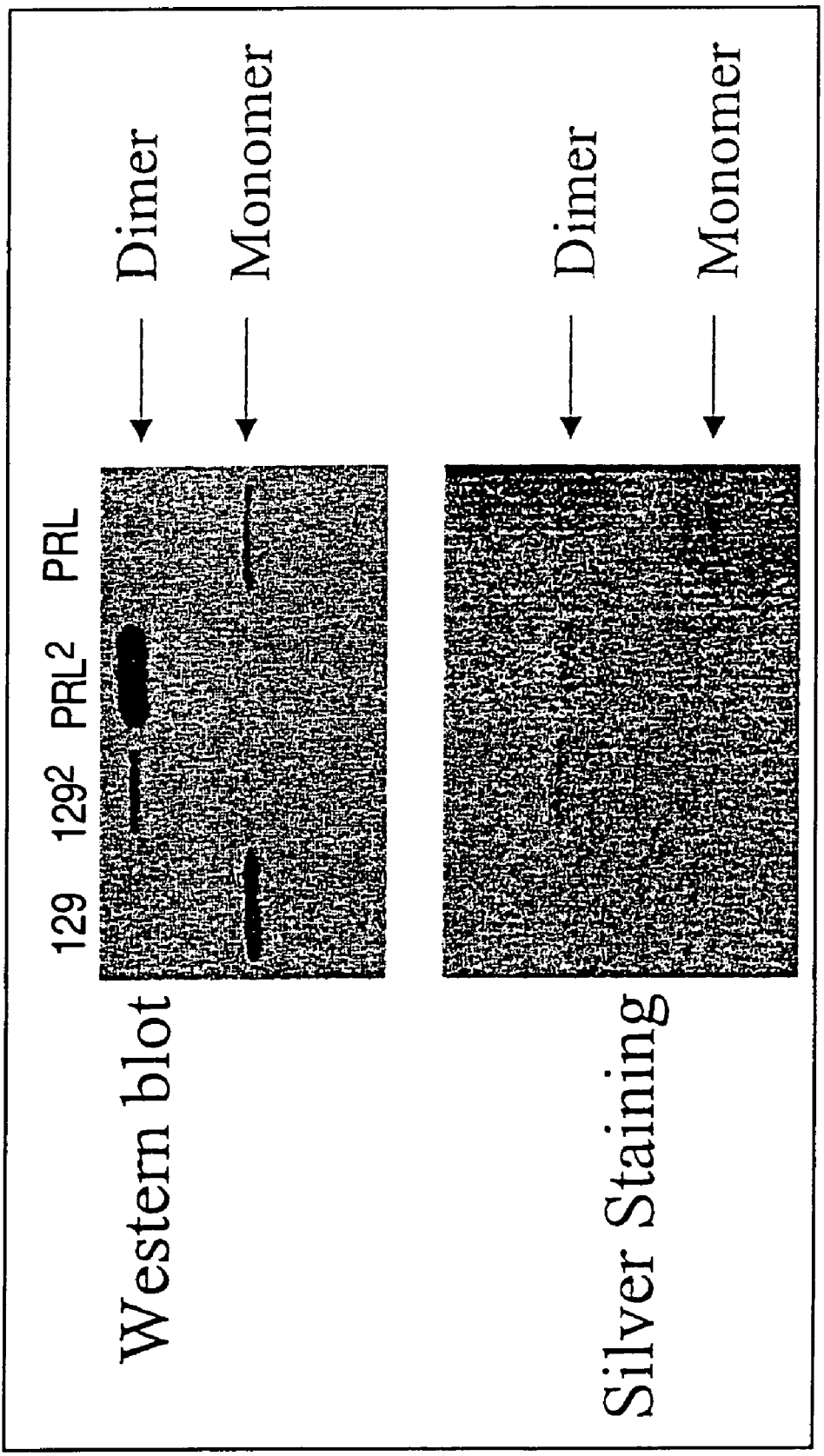
FIG. 1. Western blot and silver staining analysis of the wild-type hPRL homodimer and hPRL-G129R homodimer.

It is generally accepted that the initial step of signal transduction for human growth hormone (hGH) as well as for human prolactin (hPRL) is binding to their respective receptors. The binding process is reported to be sequential: one ligand binds to the first receptor through its first binding site (site 1) with high affinity and then finds its second receptor through its second binding site (site 2) with lower affinity resulting in a one ligand/two receptor complex. This ligand-induced dimerization of the receptors is essential for hGH and hPRL signal transduction. An amino acid substitution mutation in binding site 2 of either hGH or hPRL results in mutants with antagonistic effects both in vitro and in vivo.

In an attempt to generate a more potent hormone antagonist with a longer serum half-life, the inventor generated receptor antagonist multimers and receptor agonist multimers. Surprisingly, the inventor found that receptor antagonist homodimers, as well as the receptor agonist homodimers, act in every aspect as a receptor agonist. As long as two or more fully functional binding sites are available to bind the receptor, the ligand will act as a receptor agonist. Moreover, the receptor antagonist homodimers and receptor agonist homodimers have a prolonged serum half-life compared to their respective monomers. Also unexpectedly, the overall size of the ligand did not appear to be a crucial factor to inducing signal transduction.

Definitions

A receptor antagonist monomer is a ligand that specifically binds to a receptor. Upon binding to the receptor, the receptor antagonist monomer acts as an inhibitor of one or more cellular processes. For example, the receptor antagonist monomer can be a prolactin receptor antagonist monomer or GH receptor antagonist monomer.

A receptor antagonist multimer comprises more than one receptor antagonist monomer. The receptor antagonist monomers of the multimer need not all be the same, but may comprise at least two different receptor antagonist monomers.

A receptor antagonist multimer that is a receptor antagonist dimer comprises two receptor antagonist monomers.

A receptor antagonist homodimer comprises two of the same receptor antagonist monomers.

A receptor antagonist heterodimer comprises one different receptor antagonist monomer.

A receptor agonist monomer is a ligand that specifically binds to a receptor. Upon binding to the receptor, the ligand acts as an agonist, by inducing signal transduction and promoting one or more cellular processes. For example, the receptor agonist monomer can be a prolactin receptor agonist monomer or GH receptor agonist monomer.

A receptor agonist multimer comprises more than one receptor agonist monomer. The receptor agonist monomers of the multimer need not all be the same, but may comprise at least two different receptor agonist monomers.

A receptor agonist multimer that is a receptor agonist dimer comprises two receptor agonist monomers.

A receptor agonist homodimer comprises two of the same receptor agonist monomers.

A receptor agonist heterodimer comprises one different receptor agonist monomer.

A receptor binding multimer comprises more than one receptor monomer. The receptor monomer may be a receptor agonist monomer or a receptor antagonist monomer. The receptor binding multimer may comprise only receptor antagonist monomers, only receptor agonist monomers or a combination of receptor agonist and receptor antagonist monomers.

Compositions of the Invention

Overview

Point mutations made to a ligand's receptor binding site will interfere with the ligand's ability to interact properly with its cognate receptor and therefore initiate a signal transduction cascade. The compositions described herein comprise a ligand that, as a monomer, acts as an antagonist upon specific binding to a receptor, and as a multimer, acts as an agonist. As long as the requisite receptor binding sites on the receptor antagonist multimer are available, the multimer will act as a receptor agonist. In other words, as long as two or more functional receptor binding sites are available on the receptor antagonist multimer, the receptor antagonist multimer will act as a receptor agonist. Additionally, such a multimer has enhanced stability over its monomer, as measured by a longer serum half-life.

In a related vein, a receptor agonist multimer is described herein. Such a composition comprises a ligand that, as a monomer, acts as an agonist upon specific binding to a receptor, and as a multimer, also can induce signal transduction, despite the increase in ligand size compared to the monomer. As long as two or more functional receptor binding sites are available on the receptor agonist multimer, the receptor agonist multimer will act as a receptor agonist and induce cell signaling. The receptor agonist multimer of the present invention also exhibits an increase in stability compared to its monomer. For example, a wild-type (wt) prolactin homodimer has a longer serum half-life when compared to the wt prolactin monomer. Also, the overall increase in size of the ligand (46 kDa dimer as opposed to a 23 kDa monomer) does not preclude receptor binding.

Another embodiment of the present invention is a receptor binding multimer that comprises at least one receptor antagonist monomer and at least one receptor agonist monomer. Such a multimer also has a longer serum half-life when compared to its monomers. While this multimer may have more than two fully functional receptor binding sites, the receptor binding multimer functions as a receptor agonist.

Receptor Antagonist Monomer and Receptor Agonist Monomer

A receptor antagonist monomer, as described herein, is a ligand that specifically binds to a receptor, whereupon binding to the receptor, the receptor antagonist monomer acts as an antagonist, by inhibiting one or more cellular processes. For example, the receptor antagonist monomer can be a prolactin receptor antagonist monomer or GH receptor antagonist monomer. If the receptor antagonist monomer is a prolactin receptor antagonist monomer, it is preferred that the prolactin receptor antagonist monomer has an amino acid substitution at a position corresponding to 129 in hPRL. Still more preferred, the prolactin receptor antagonist monomer comprises a Gly to Arg substitution at a position corresponding to 129 in hPRL (hPRL-G129R). If the receptor antagonist monomer is a growth hormone receptor antagonist monomer, it is preferred that the growth hormone receptor antagonist monomer has an amino acid substitution at a position corresponding to 120 in hGH. Still more preferred, the growth hormone receptor antagonist monomer comprises a Gly to Arg substitution at a position corresponding to 120 in hGH (hGH-G129R).

Similarly, a receptor agonist monomer is a ligand that specifically binds to a receptor, whereupon binding to the receptor, the ligand acts as an agonist, inducing signal transduction and promoting one or more cellular processes. In a preferred embodiment, the receptor agonist monomer is selected from the group consisting of a prolactin receptor agonist monomer and a growth hormone receptor agonist monomer. If the receptor agonist monomer is a prolactin receptor agonist monomer, it is preferred that the prolactin receptor agonist monomer is wt hPRL. If the receptor agonist monomer is a growth hormone receptor agonist monomer, it is preferred that the growth hormone receptor agonist monomer is wt hGH.

Receptor Antagonist Multimer and Receptor Agonist Multimer

A receptor antagonist multimer comprises at least two receptor antagonist monomers. The receptor antagonist multimer acts as a receptor agonist. A receptor agonist is a ligand that specifically binds to a receptor and, upon binding to the receptor, acts as an agonist, inducing signal transduction and promoting one or more cellular processes.

A receptor agonist multimer comprises at least two receptor agonist monomers. The receptor agonist multimer acts as a receptor agonist, irrespective of the increased ligand size, and induces signal transduction and promotes one or more cellular processes.

A receptor antagonist multimer that comprises two receptor antagonist monomers is a receptor antagonist dimer. Likewise, a receptor agonist multimer that comprises two receptor agonist monomers is a receptor agonist dimer. The receptor antagonist monomers or receptor agonist monomers of the receptor antagonist multimer or receptor agonist multimer, respectively, need not all be the same. For example, the receptor antagonist multimer may comprise at least one different receptor antagonist monomer and the receptor agonist multimer may comprise at least one receptor agonist monomer. A receptor antagonist multimer or receptor agonist multimer that comprises all the same receptor antagonist or agonist monomers is a homologous multimer. For example, a receptor antagonist multimer that comprises two of the same receptor antagonist monomers is a receptor antagonist homodimer.

A receptor antagonist multimer or receptor agonist multimer that comprises at least one different receptor antagonist monomer or receptor agonist monomer, respectively, is a heterologous multimer. For example, a receptor antagonist heterodimer comprises one different receptor antagonist monomer.

Prolactin Receptor Antagonist Multimers

Cell signaling via prolactin is initiated by prolactin binding to the prolactin receptor (PRLR). This binding induces dimerization of the prolactin receptor, thereby triggering a signal transduction cascade. Signal transduction in the prolactin signaling pathway involves signal transducers and activators of transcription (STAT) phosphorylation. When a prolactin antagonist (PRLA) binds to the prolactin receptor STATs will not be phosphorylated and the autocrine/paracrine effects of endogenous PRL will not be observed.

A suitable prolactin receptor antagonist monomer contemplated by the invention generally will retain the characteristic of specific binding to the PRLR, yet will have some structural deficiency that disrupts the normal PRL cell signaling pathway. Such a structural deficiency includes those that disrupt PRL (and thus PRLR) dimerization. Such a structural deficiency can be a substitution of Gly to Arg at a position corresponding to 129 in hPRL (denoted as hPRL-G129R).

A species comparison of amino acid sequences within the third α-helical region of PRLs, shown in Table 1.

A species comparison of amino acid sequences within the third α-helical region of PRLs, shown in Table 1.

hPRL is invariable among PRLs, suggesting an important role in its function. Thus, substituting any amino acid for Gly 129 should create a prolactin receptor antagonist from prolactin in each of these species (Chen et al., *Molec. Endocrinol.* (1995)). In one embodiment, a prolactin receptor antagonist monomer is created by substituting a relatively bulky side chain amino acid, such as Arg, for Gly 129. Therefore, one aspect of the invention contemplates conservative variants of PRL that are characterized by the presence of a relatively small side-chain amino acid (i.e. Gly) at a specific position, wherein the small side-chain amino acid is changed to a bulky side-chain amino acid, creating an antagonistic form of the

TABLE 1

| Species | Domain | Peptide Sequence | 129 | Pep. Seq. | SEQ ID NO. |
|---|---|---|---|---|---|
| Human | PRL | IEEQTKRLLR | G | MELIVS-QVHP | SEQ ID NO. 1 |
| Rat | PRL | IEEQNKRLLE | G | IEKIIG-QAYP | SEQ ID NO. 2 |
| Mouse | PRL | IEEQNKQLLE | G | VEKIIS-QAYP | SEQ ID NO. 3 |
| Hamster | PRL | IGEQNKRLLE | G | IEKILG-QAYP | SEQ ID NO. 4 |
| Fin whale | PRL | EEEENKRLLE | G | MEKIVG-QVHP | SEQ ID NO. 5 |
| Mink | PRL | IEEENRRLLE | G | MEKIVG-QVHP | SEQ ID NO. 6 |
| Cattle | PRL | IEEQNKRLIE | G | MEMIFG-QVIP | SEQ ID NO. 7 |
| Sheep | PRL | EEEENKRLLE | G | MENIFG-QVIP | SEQ ID NO. 8 |
| Pig | PRL | IEEQNKRLLE | G | MEKIVG-QVHP | SEQ ID NO. 9 |
| Camel | PRL | IEEQNKRLLE | G | MEKIVG-QVHP | SEQ ID NO. 10 |
| Horse | PRL | EIEQNRRLLE | G | MEKIVG-QVQP | SEQ ID NO. 11 |
| Elephant | PRL | VKEENQRLLE | G | IEKIVD-QVHP | SEQ ID NO. 12 |
| Ancestral mammal | PRL | IEEENKRLLE | G | MEKIVG-QVHP | SEQ ID NO. 13 |
| Chicken | PRL | IEEQNKRLLE | G | MEKIVG-RVHS | SEQ ID NO. 14 |
| Turkey | PRL | IEEQDKRLLE | G | MEKIVG-RIHS | SEQ ID NO. 15 |
| Sea turtle | PRL | IEEQNKRLLE | G | MEKIVG-QVHP | SEQ ID NO. 16 |
| Crocodile | PRL | IEEQNKRLLE | G | MEKIIG-RVQP | SEQ ID NO. 17 |
| Alligator | PRL | IEEQNKRLLE | G | MEKVIG-RVQP | SEQ ID NO. 18 |
| Ancestral amniote | PRL | IEEQNKRLLE | G | MEKIVG-QVHP | SEQ ID NO. 19 |
| Xenopus | PRL | VEEQNKRLLE | G | MEKIVG-RIHP | SEQ ID NO. 20 |
| Bullfrog | PRL | VEEQTKRLLE | G | MERIIG-RIQP | SEQ ID NO. 21 |
| Lungfish | PRL | VEDQTKQLIE | G | MEKILS-RMHP | SEQ ID NO. 22 |
| Tilapia | PRL | MQQYSKSLKD | G | LD-VLSSKMGS | SEQ ID NO. 23 |
| Tilapia | PRL | MQEHSKDLKD | G | LD-ILSSKMGP | SEQ ID NO. 24 |
| Common carp | PRL | LQENINSLGA | G | LEHVF-NKMDS | SEQ ID NO. 25 |
| Bighead carp | PRL | LQDNINSLGA | G | LERVV-HKMGS | SEQ ID NO. 26 |
| Silver carp | PRL | LQDNINSLVP | G | LEHVV-HKMGS | SEQ ID NO. 27 |
| Chun salmon | PRL | LQDYSKSLGD | G | LD-IMVNKMGP | SEQ ID NO. 28 |
| Chinook salmon | PRL | LQDYSKSLGD | G | LD-IMVNKMGP | SEQ ID NO. 29 |
| Trout | PRL | LQDYSKSLGD | G | LD-IMVNKMGP | SEQ ID NO. 30 |
| Species | Domain | Peptide Sequence | 120 | Pep. Seq. | SEQ ID NO. |
| Human | GH | VYDLLKDLEE | G | IQTLMRELEDG | SEQ ID NO. 31 |
| Bovine | GH | VYEKLKDLEE | G | ILALMRELEDG | SEQ ID NO. 32 |

In a preferred embodiment, the receptor antagonist multimer comprises a prolactin receptor antagonist monomer. Preferably, the receptor antagonist multimer is a prolactin receptor antagonist homodimer. More preferably, the prolactin receptor antagonist homodimer comprises a prolactin receptor antagonist monomer that has an amino acid substitution at a position corresponding to 129 in hPRL. Most preferably, the prolactin receptor antagonist multimer is a hPRL-G129R homodimer. Surprisingly the prolactin receptor antagonist multimer acts as a prolactin agonist, with a longer half-life than the prolactin receptor antagonist monomer. This result suggests that as long as two or more binding sites (site 1 plus another site 1 in hPRL-G129R homodimer) are available in the multimer, the ligand serves as an agonist.

It is noted that other prolactin antagonists are suitable prolactin receptor antagonist monomers for use in the present invention. According to Table 1, it is clear that Gly 129 of protein. Such a prolactin receptor antagonist monomer is suitable for making the receptor antagonist multimer described herein.

The prolactin receptor antagonist monomers of the present invention also include conservative variants of the prolactin receptor antagonist monomers discussed herein. The overall structure and composition of the receptor antagonist monomer, in that respect, are important only insofar as they confer the appropriate functional characteristics, i.e., receptor agonism when made multimeric and enhanced stability compared to its respective monomer.

Conservative variants according to the invention generally conserve the overall molecular structure of the protein domains. Given the properties of the individual amino acids comprising the disclosed protein products, some rational substitutions will be apparent. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) serine and threonine; (ii) proline and glycine; and (iii) alanine, valine, leucine and isoleucine. Given the known genetic code, and recombinant and synthetic DNA techniques, the skilled scientist readily can construct DNAs encoding the conservative amino acid variants.

Conservative variants specifically contemplate truncations of the presently described receptor antagonist monomers. Truncations may be made from the N- or C-terminus, but generally do not entail deleting more than about 30% of the native molecule. More preferably, less than about 20%, and most preferably, less than about 10% of the native molecule is deleted.

In general, both the DNA and protein molecules of the invention can be defined with reference to "sequence identity. Some molecules have at least about 50%, 55% or 60% identity. Preferred molecules are those having at least about 65% sequence identity, more preferably at least 65% or 70% sequence identity. Other preferred molecules have at least about 80%, more preferably at least 80% or 85%, sequence identity. Particularly preferred molecules have at least about 90% sequence identity, more preferably at least 95% sequence identity. As used herein, two nucleic acid molecules or proteins are said to "share significant sequence identity" if the two contain regions which possess greater than 85% sequence (amino acid or nucleic acid) identity. Accordingly, suitable receptor antagonist monomers for the present invention share greater than 85% sequence (amino acid or nucleic acid) identity with the receptor antagonist monomers described herein.

"Sequence identity" is defined herein with reference the Blast 2 algorithm, which is available at the NCBI (http://www.ncbi.nlm.nih.gov/BLAST), using default parameters. References pertaining to this algorithm include: those found at http://www.ncbi.nlm.nih.gov/BLAST/blast_references.html; Altschul, S. F., Gish, W., Miller, W., Myers, E. W. & Lipman, D. J. (1990) "Basic local alignment search tool." J. Mol. Biol. 215: 403-410; Gish, W. & States, D. J. (1993) "Identification of protein coding regions by database similarity search." Nature Genet. 3: 266-272; Madden, T. L., Tatusov, R. L. & Zhang, J. (1996) "Applications of network BLAST server" Meth. Enzymol. 266: 131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25: 3389-3402; and Zhang, J. & Madden, T. L. (1997) "PowerBLAST: A new network BLAST application for interactive or automated sequence analysis and annotation." Genome Res. 7: 649-656. Accordingly, the prolactin peptide sequences from different species, which include those listed in Table 1, can be aligned, using standard computer programs like BLAST, to inform further variation in prolactin-derived receptor antagonists that preserve their essential function.

Prolactin Receptor Agonist Multimer

A suitable prolactin receptor agonist monomer for the prolactin receptor agonist multimer contemplated herein, generally will retain the characteristic of specific binding to the PRLR. Although the prolactin receptor agonist multimer will be larger than the prolactin receptor agonist monomer, the normal PRL cell signaling pathway will not be disrupted.

In a preferred embodiment, the receptor agonist multimer comprises a wild-type prolactin receptor agonist monomer. Preferably, the receptor agonist multimer is a prolactin receptor agonist homodimer. More preferably, the prolactin receptor agonist multimer is a wt-hPRL homodimer. The prolactin receptor agonist multimer described herein acts as an agonist and exhibits a longer half-life than the prolactin receptor agonist monomer. This characteristic suggests that as long as there are two or more fully functional binding sites (site 1 plus site 2 in wild type hPRL monomer; four binding sites in the wt-hPRL homodimer) available in the multimer, the ligand will act as an agonist. Similarly, a receptor binding multimer is also contemplated that, for example, comprises a wt-hPRL and a hPRL-G129R monomer.

The prolactin receptor agonist monomers of the present invention also include conservative variants of the prolactin receptor agonist monomers discussed herein. The overall structure and composition of the receptor agonist monomer, in that respect, is important only insofar as it confers the appropriate functional characteristics, i.e., receptor agonism when made multimeric and enhanced stability when compared to its respective monomer. It is also contemplated suitable receptor agonist monomers for the present invention share greater than 85% sequence (amino acid or nucleic acid) identity with the receptor agonist monomers described herein.

Growth Hormone Receptor Antagonist Multimer

In a related vein, a growth hormone receptor antagonist multimer is described. Cell signaling via growth hormone is initiated by growth hormone binding to the growth hormone receptor. This binding induces dimerization of the growth hormone receptor, thereby triggering a signal transduction cascade in cells comprising a growth hormone bound receptor. Signal transduction in the growth hormone signaling pathway involves signal transducers and activators of transcription (STAT) phosphorylation. Accordingly, growth hormone receptor antagonist binding to the growth hormone receptor will not result in STAT phosphorylation and therefore the autocrine/paracrine effects of endogenous growth hormone will not be observed.

In a preferred embodiment, the receptor antagonist multimer comprises a growth hormone receptor antagonist monomer. Preferably, the growth hormone receptor antagonist multimer is a growth hormone receptor antagonist homodimer. More preferably, the growth hormone receptor antagonist monomer of the growth hormone receptor antagonist homodimer has an amino acid substitution at a position corresponding to 120 in hGH. Most preferably, the growth hormone receptor antagonist multimer is a hGH-G120R homodimer. It should be noted that the growth hormone receptor antagonist monomers described in U.S. Pat. No. 5,350,836, U.S. Pat. No. 5,681,809 and U.S. Pat. No. 5,958,879 are also suitable monomers for the present invention and the aforementioned patents are hereby incorporated herein in their entirety. Surprisingly the growth hormone receptor antagonist multimer acts as a growth hormone agonist and has a longer half-life than its growth hormone receptor antagonist monomer. This result suggests that as long as there are at least two binding sites (site 1 plus another site 1 in hGH-G120R homodimer) available in the multimer, the multimer serves as an agonist.

Other growth hormone antagonists are suitable growth hormone receptor antagonist monomers for the receptor antagonist multimer of the present invention. In one embodiment, a growth hormone receptor antagonist monomer is created by substituting a relatively bulky side chain amino acid, such as Arg for Gly. Therefore, one aspect of the invention contemplates conservative variants of growth hormone that are characterized by the presence of a relatively small side-chain amino acid (i.e. Gly) at a specific position, wherein the small side-chain amino acid is replaced with a bulky side-chain amino acid, creating an antagonistic form of the protein. Such a growth hormone receptor antagonist monomer is suitable for making the receptor antagonist multimer described herein.

The growth hormone receptor antagonist monomers of the present invention also include conservative variants of the growth hormone receptor antagonist monomers discussed herein. The overall structure and composition of the receptor antagonist monomer, in that respect, is important only insofar as it confers the appropriate functional characteristics, i.e., receptor agonism when made multimeric and enhanced stability when compared to its respective monomer. It is also contemplated that suitable receptor antagonist monomers for the present invention share greater than 85% sequence (amino acid or nucleic acid) identity with the receptor antagonist monomers described herein.

Growth Hormone Receptor Agonist Multimer

A suitable growth hormone receptor agonist monomer for the growth hormone receptor agonist multimer contemplated herein, will generally retain the characteristic of specific binding to the growth hormone receptor. Although the growth hormone receptor agonist multimer will be larger than the growth hormone receptor agonist monomer, the normal GH cell signaling pathway will not be disrupted.

In a preferred embodiment, the receptor agonist multimer comprises a wild-type growth hormone receptor agonist monomer. Preferably, the receptor agonist multimer is a growth hormone receptor agonist homodimer. More preferably, the growth hormone receptor agonist multimer is a wt-hGH homodimer. The growth hormone receptor agonist multimer described herein acts as an agonist and exhibits a longer half-life than the growth hormone receptor agonist monomer. This characteristic suggests that as long as there are at least two binding sites (site 1 plus site 2 in wild type hGH monomer; four binding sites in the wild-type hGH homodimer) available in the multimer, the multimer acts as an agonist. Similarly, a receptor binding multimer is also contemplated that, for example, comprises a wt-hGH and a hGH-G120R monomer.

The growth hormone receptor agonist monomers of the present invention also include conservative variants of the growth hormone receptor agonist monomers discussed herein. The overall structure and composition of the receptor agonist monomer, in that respect, are important only insofar as they confer the appropriate functional characteristics, i.e., receptor agonism when made multimeric and enhanced stability when compared to its respective monomer. It is also contemplated that suitable receptor antagonist monomers for the present invention share greater than 85% sequence (amino acid or nucleic acid) identity with the receptor antagonist monomers described herein.

Other Suitable Receptor Binding Multimers

The receptor binding multimers described herein are exemplary and are not intended to limit in any way the scope of suitable receptor antagonist monomers or receptor agonist monomers for use in the receptor binding multimers of the present invention. It is recognized that ligands other than prolactin and growth hormone, that bind to their cognate receptors by a mechanism similar to prolactin and growth hormone (i.e., multiple receptor binding sites on the ligand with varying affinities for the receptor) may also be made multimeric. Such receptor binding multimers would also act as an agonist and have a prolonged serum half-life.

Therapeutic Compositions

In a related vein, a pharmaceutical composition comprising a therapeutically useful amount of a receptor binding multimer, such as a receptor antagonist multimer or receptor agonist multimer, and a pharmaceutically suitable excipient is contemplated. The receptor binding multimer may comprise more than one receptor antagonist monomer, more than one receptor agonist monomer, or a combination of receptor agonist and receptor antagonist monomers. In a preferred embodiment, the receptor antagonist monomer is selected from the group consisting of a prolactin receptor antagonist monomer and a growth hormone receptor antagonist monomer, and the receptor agonist monomer is selected from the group consisting of a prolactin receptor agonist monomer and a growth hormone receptor agonist monomer. In a preferred embodiment, the receptor antagonist multimer or receptor agonist multimer is a dimer. Most preferably, the receptor antagonist multimer or receptor agonist multimer is a homodimer.

The receptor binding multimers of the present invention can be formulated according to known methods to prepare pharmaceutically useful compositions, whereby the inventive molecules, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences*(16th ed., Osol, A., Ed., Mack, Easton Pa. (1980)). In order to form a pharmaceutically acceptable composition suitable for effective administration, such compositions will contain an effective amount of one or more of the proteins of the present invention, together with a suitable amount of carrier vehicle.

Pharmaceutical compositions for use in accordance with the present invention may be formulated in conventional manner using one or more physiologically acceptable carriers or excipients. Thus, the multimers may be formulated for administration by inhalation or insufflation (either through the mouth or the nose) or oral, subcutaneous, intramuscular, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the composition may take the form of tablets or lozenges formulated in conventional manner.

In addition to the formulations described previously, the multimers of the present invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For administration by inhalation, the receptor antagonist or agonist multimers for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The receptor antagonist or agonist multimers may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Methods of the Invention

Method for Inducing Cell Signaling

Contemplated in the present invention is a method for increasing prolactin cell signaling comprising administering to a patient an effective amount of a protein comprising a prolactin multimer, such as a prolactin receptor antagonist multimer or a prolactin receptor agonist multimer. Preferably, the prolactin receptor antagonist multimer or prolactin receptor agonist multimer is a homodimer. Also preferred is that the prolactin receptor agonist multimer is a wt-hPRL homodimer. In another embodiment, the prolactin receptor antagonist multimer is a prolactin receptor antagonist homodimer. Preferably, the prolactin receptor antagonist homodimer comprises a prolactin receptor antagonist monomer that has an amino acid substitution at a position corresponding to 129 in hPRL. Most preferably, the prolactin receptor antagonist homodimer is a hPRL-G129R homodimer.

Also considered herein is a prolactin multimer, wherein the prolactin multimer comprises a prolactin receptor antagonist monomer and a prolactin receptor agonist monomer. For example, a prolactin multimer that comprises a wild-type hPRL monomer and hPRL-G129R monomer is contemplated.

In another embodiment of the present invention is a method for increasing growth hormone cell signaling comprising administering to a patient an effective amount of a protein comprising a growth hormone multimer, such as a growth hormone receptor antagonist multimer or growth hormone receptor agonist multimer. Preferably, the growth hormone receptor antagonist multimer or growth hormone receptor agonist multimer is a homodimer. Also preferred is that the growth hormone receptor agonist multimer is a wild-type hGH homodimer. Still preferred, the growth hormone receptor antagonist homodimer comprises a growth hormone receptor antagonist monomer that has an amino acid substitution at a position corresponding to 120 in hGH. For example, the growth hormone receptor antagonist homodimer is a hGH-G120R homodimer.

Also considered herein is a growth hormone multimer, wherein the growth hormone multimer comprises a growth hormone receptor antagonist monomer and a growth hormone receptor agonist monomer. For example, a growth hormone multimer that comprises a wild-type hGH monomer and hGH-G120R monomer is contemplated.

Methods of Enhancing Protein Stability

Described herein is a method of increasing protein stability comprising making a receptor binding multimer that comprises at least two receptor antagonist monomers, at least two receptor agonist monomers or at least one receptor antagonist monomer and at least one receptor agonist monomer. For example, the method of increasing protein stability may comprise making a protein that comprises a wild-type prolactin monomer and a hPRL-G129R monomer. Such a multimer will have an increased half life when compared to each of its monomers. It is also considered that a receptor binding multimer need not be composed only of identical monomers, e.g., all be prolactin receptor agonist monomers or growth hormone receptor agonist monomers. In fact, a receptor binding multimer may comprise one prolactin receptor agonist monomer and one growth hormone receptor agonist monomer.

In a preferred embodiment, the hormone is prolactin or growth hormone. For example, the receptor antagonist monomer can be a prolactin receptor antagonist monomer or a growth hormone receptor antagonist monomer and the receptor agonist monomer can be a wild-type prolactin monomer or a growth hormone prolactin monomer.

It is also considered that the prolactin and growth hormone receptor antagonist monomers of the present method comprise an amino acid substitution at position 129 in hPRL and 120 in hGH, respectively. Most preferably, the invention described herein contemplates a method of increasing hormone stability comprising making a protein that comprises a hPRL-G129R homodimer or hGH-G120R homodimer.

Methods of Treatment

Contemplated herein is a method of treating a disease, disorder, or condition comprising administering to a patient a therapeutically effective amount of a protein comprising a receptor binding multimer, such as a receptor antagonist multimer or receptor agonist multimer. In a preferred embodiment, the receptor binding multimer may be a prolactin receptor binding multimer or a growth hormone receptor binding multimer. An exemplary receptor antagonist multimer is a prolactin receptor antagonist multimer or a growth hormone receptor antagonist multimer. Such a receptor antagonist multimer comprises a prolactin or growth hormone receptor antagonist monomer. Preferably, a prolactin or growth hormone receptor antagonist monomer comprises an amino acid substitution at position corresponding to 129 in hPRL and 120 in hGH, respectively. Also preferred, the prolactin or growth hormone receptor antagonist multimer is a homodimer. For example, a hPRL-G129R homodimer and a hGH-G120R homodimer are contemplated herein.

In another embodiment, the receptor agonist multimer is a prolactin receptor agonist multimer or growth hormone receptor agonist multimer. For example, the prolactin and growth hormone receptor agonist multimers may comprise a wild-type prolactin or growth hormone monomer, respectively. Preferably, the prolactin and growth hormone multimers are wild-type hPRL and wild-type hGH homodimers, respectively.

Also considered herein is a method of treating a disease, disorder, or condition comprising administering to a patient a therapeutically effective amount of a receptor binding multimer, that comprises at least one receptor antagonist monomer and at least one receptor agonist monomer. For example, a receptor binding multimer that comprises a growth hormone receptor agonist monomer and a growth hormone receptor antagonist monomer or a prolactin receptor antagonist monomer and a prolactin receptor agonist monomer is contemplated.

Therapeutic methods involve administering to a patient in need of a treatment a therapeutically effective amount of the receptor antagonist or agonist multimer. "Therapeutically effective" is employed here to denote the amount of receptor antagonist or receptor agonist multimer that is sufficient to induce cell signaling with a longer half life. The patient may be a human or non-human animal.

Administration during in vivo treatment may be via any number of routes, including parenteral and oral, but preferably subcutaneous injection. Intracapsular, intravenous, intramuscular, subcutaneous, intrathecal and intraperitoneal routes of administration may also be employed. The skilled artisan will recognize that the route of administration will vary depending on the disorder to be treated.

Determining a therapeutically effective amount specifically will depend on such factors as toxicity and efficacy of the medicament. Toxicity may be determined using methods well known in the art. A pharmaceutically effective amount, therefore, is an amount that is deemed by the clinician to be toxicologically tolerable, yet efficacious.

The prolactin receptor antagonist and agonist multimers of the present invention can be used to treat a disease, disorder, or condition resulting from either decreased circulating or functional prolactin levels. It is also considered that the prolactin receptor antagonist and agonist multimers can be used any time prolactin cell signaling is desired. For example, the prolactin receptor antagonist and agonist multimers may be used for treating the following exemplary diseases, disorders, or conditions including, but not limited to, immunodepression, supplementing ovarian stimulation for in vitro fertilization and restoring normal sperm in infertile men. Prolactin can also to potentiate immunohematopoietic function and therefore can also be used for treating a disease, disorder or condition that presents with aberrant or suboptimal immune function. The prolactin receptor antagonist multimer and prolactin receptor agonist multimer will exhibit greater stability, as measured by half-life, when compared to the prolactin receptor antagonist and prolactin receptor agonist monomers, respectively.

The growth hormone receptor antagonist and growth hormone receptor agonist multimers of the present invention can be used to treat a disease or disorder resulting from growth hormone diminished or deficient states. An exemplary disease, disorder or condition includes, but is not limited to dwarfism. For example, it is also considered that the growth hormone receptor antagonist multimers and growth hormone receptor agonist multimers can be used to treat osteoporosis, congestive heart failure, frailty associated with aging, obesity, accelerating bone fracture repair, attenuating protein catabolic response after a major operation, reducing cachexia and protein loss due to chronic illness, accelerating wound healing, or accelerating the recovery of burn patients or patients having undergone major surgery, improving muscle strength, mobility, maintenance of skin thickness, metabolic homeostasis or renal homeostasis. The growth hormone receptor antagonist multimers and growth hormone receptor agonist multimers of the present invention will exhibit greater stability, as measured by half-life, when compared to the growth hormone receptor antagonist monomers and growth hormone receptor agonist monomers, respectively.

Methods of Making

The present invention is not limited to any particular method of producing the receptor binding multimers contemplated herein. According to the contemplated recombinant methods of production, however, the present invention provides recombinant DNA constructs comprising one or more of the nucleotide sequences described in the present invention. The recombinant constructs of the present invention comprise a vector, such as a plasmid or viral vector, into which a DNA or DNA fragment, typically bearing an open reading frame, is inserted, in proper orientation to allow expression from a promoter. The promoter may be present in the vector or may be part of the DNA that is inserted into the vector. The cDNA encoding a receptor binding multimer should be in head to tail tandem sequences. The present invention further contemplates cells containing these vectors.

In another embodiment of the present invention is a method of making a receptor agonist comprising designing a cDNA encoding a receptor antagonist multimer which links the C terminus of the first receptor antagonist monomer with the N terminus of the second receptor antagonist monomer. Preferably, at least the first receptor antagonist monomer is a prolactin receptor antagonist monomer or a growth hormone receptor antagonist monomer. In a preferred embodiment, the prolactin receptor antagonist monomer and the growth hormone receptor antagonist monomer comprise an amino acid substitution at position corresponding to 129 in hPRL and 120 in hGH, respectively. Also preferred, the prolactin receptor antagonist monomer is hPRL-G129R monomer and the growth hormone receptor antagonist monomer is hGH-G120R monomer.

Similarly, a method of making a receptor agonist comprising designing a cDNA encoding a receptor agonist multimer which links the C terminus of the first receptor agonist monomer with the N terminus of the second receptor agonist monomer, is also contemplated. Preferably, at least the first receptor agonist monomer is selected from the group consisting of a prolactin receptor agonist monomer and a growth hormone receptor agonist monomer. In a preferred embodiment, the prolactin receptor agonist monomer and the growth hormone receptor agonist monomer are wild-type hPRL and wild-type hGH, respectively.

In a related vein, a method of making a receptor agonist comprising designing a cDNA encoding a receptor binding multimer which links the C terminus of a receptor agonist monomer with the N terminus of a receptor antagonist monomer, is also described. Preferably, at least the receptor agonist monomer is a prolactin receptor agonist monomer or a growth hormone receptor agonist monomer, such as wild-type hPRL or wild-type hGH, respectively, and the receptor antagonist monomer is a prolactin receptor antagonist monomer or a growth hormone receptor antagonist monomer. In a preferred embodiment, the receptor binding multimer comprises a wild-type prolactin receptor agonist monomer and a hPRL-G129R antagonist monomer.

Expression Systems

Contemplated in the present invention is a DNA construct comprising the nucleotide sequence of the receptor antagonist multimer. In a preferred embodiment, the receptor antagonist monomer comprises a prolactin receptor antagonist monomer or growth hormone receptor antagonist monomer. Also preferred, the receptor antagonist multimer is a homodimer. For example a DNA construct comprising a hPRL-G129R homodimer or hGH-G120R homodimer nucleotide sequence is considered herein.

In a related vein, a DNA construct comprising the nucleotide sequence of the receptor agonist multimer is also described. In a preferred embodiment, the receptor agonist multimer comprises a prolactin receptor agonist monomer or a growth hormone receptor agonist monomer. Also preferred, the receptor agonist multimer is a homodimer. For example a DNA construct comprising a wild-type hPRL homodimer or wild-type hGH homodimer nucleotide sequence is considered herein.

Similarly, a DNA construct comprising the nucleotide sequence of a receptor binding multimer that comprises at least one receptor agonist monomer and one receptor antagonist monomer. Preferably, the receptor binding multimer comprises a prolactin receptor agonist monomer and a prolactin receptor antagonist monomer. For example, a DNA construct comprising the nucleotide sequence of a receptor binding multimer that comprises a wild-type hPRL monomer and a hPRL-G129R monomer is considered. Also preferred is a DNA construct comprising the nucleotide sequence of a receptor binding multimer that comprises a wild-type hGH monomer and a hGH-G120R monomer.

Recombinant protein production is well known in the art and is outlined briefly below.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may, also be employed as a matter of choice. In a preferred embodiment, the prokaryotic host is *E. coli*. Still more preferred, the *E. coli* expression vector is pET22b.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotec, Madison, Wis., U.S.A), pBs, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia). A preferred vector according to the invention is the Pt71 expression vector (Paris et al., *Biotechnol. Appl. Biochem.* 12: 436-449 (1990)).

These "backbone" sections are combined with an appropriate promoter and the structural sequence to be expressed. Bacterial promoters include lac, T3, T7, lambda $P_R$ or $P_L$, trp, and ara. T7 is the preferred bacterial promoter.

Following transformation of a suitable host strain and growth of the host strain to an appropriate cell density, the selected promoter is derepressed/induced by appropriate means (e.g., temperature shift or chemical induction) and cells are cultured for an additional period. Cells are typically harvested by centrifugation, disrupted by physical or chemical means, and the resulting crude extract retained for further purification.

Various mammalian cell culture systems can also be employed to express recombinant protein. Examples of mammalian expression systems include selected mouse L cells, such as thymidine kinase-negative (TK) and adenine phosphoribosul transferase-negative (APRT) cells. Other examples include the COS-7 lines of monkey kidney fibroblasts, described by Gluzman, *Cell* 23: 175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, early and late SV40, LTRs from retrovirus, and mouse metallothionein-I. Exemplary mammalian vectors include pWLneo, pSV2cat, pOG44, pXT1, pSG (Stratagene) pSVK3, pBPV, pMSG, and pSVL (Pharmacia). In a preferred embodiment, the mammalian expression vector is pUCIG-MET. Selectable markers include CAT (chloramphenicol transferase).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts. (E.g., See Logan et al., 1984, *Proc. Natl. Acad. Sci. USA* 81: 3655-3659).

The following examples are intended to be illustrative and not limiting

EXAMPLES

Example 1

Cloning and Construction of the Expression Plasmid pET22b-G129R-G129R and pET22b-hPRL-hPRL PCR fragments from hPRL-G129R or hPRL cDNA. Monomer A is amplified with primers containing restriction sites NdeI (at 5' end) and BamH1 (at 3' end), which contains the translational start ATG to TGC, a codon encodes amino acid Cys at position 199 that is right before the stop codon TAA followed by GGATCC (BamH1). Monomer B is amplified from AAC that encodes the amino acid Asn at position 1 with the addition of GGATCC (BamH1) to stop codon TAA followed by TCTAGA (XbaI). Next, these fragments were digested with respective restriction enzymes and ligated into pET22b an E. coli expression vector, to generate an expression plasmid that has incorporated these fragments (i.e. pET22b-G129R-G129R; or pET22b-hPRL-hPRL). A BamH1 restriction site was added for cloning purposes between two hPRL-G129R or two hPRL cDNAs, which resulted in two extra amino acid residues (Gly and Ser) at the junction of the dimers, respectively.

Example 2

Production and Purification of hPRL-G129R and wt-hPRL Homodimers hPRL-G129R and wt-hPRL homodimers were produced using an E. coli expression vector, pET22b. Briefly, BL21 (DE3) cells (Novagen; Madison, Wis.) were transformed with wt-hPRL homodimer or hPRL-G129R homodimer expression using the calcium chloride method. The transformants were spread on an ampicillin plate, and grown overnight at 37° C. An LB seed culture was inoculated with 6-10 colonies and incubated overnight. The following day, a LB culture was generated by inoculation of 5% of the seed culture and grown for ~2.5 hours at 37° C. with agitation. IPTG (Fisher Scientific; Norcross, Ga.) was then added to the culture (1 mM final concentration) to induce expression of hPRL or hPRL-G129R and the culture was incubated for an additional 4 hrs. Bacteria were pelleted and resuspended in a solution containing 0.2M $NaPO_4$ (pH 8.0), 10 mM EDTA, and 0.5% Triton X-100. The resuspended cells were lysed using a 550 Sonic Dismembrator from Fisher Scientific (Norcross, Ga.), and the products, in the form of inclusion bodies, were pelleted by centrifugation at 12,000 g for 15 min. The pellets were then resuspended in solution A [0.2M $NaPO_4$ (pH 7.0), 5 mM EDTA, 1M Urea, 0.5% Triton X-100] and pelleted by centrifugation at 12,000 g for 15 min. These pellets were then resuspended in solution B [0.2 M $NaPO_4$ (pH 8.0), 8M urea, 1% v/v beta-mercaptoethanol], and the refolding process was initiated. The refolding process consisted of dialyzing the protein against decreasing amounts of urea and beta-mercaptoethanol in the presence of 50 mM $NH_4HCO_3$ (pH 8.0) for at least three consecutive days. The protein product was then filtered through a 0.22 micron filter, degassed and purified using a Q-Sepharose anionic exchange column (Pharmacia; Piscataway, N.J.) on the FPLC system (Pharmacia; Piscataway, N.J.). The concentration of hPRL or hPRL-G129R purified from FPLC was determined using the PRL immunoradiometric assay (IRMA) kit (DPC; Los Angeles, Calif.). The purity of both PRL and hPRL-G129R exceeded 98% as determined by SDS-PAGE in combination with silver staining (Biorad; Hercules, Calif.). The endotoxin level in the final products from all batches was <5 EU/mg, as determined by Cape Cop Inc. The recombinant proteins produced by this method have an extra Met at the N-terminus as compared to wild type PRL. FIG. 1 indicates that both wt-hPRL and hPRL-G129 homodimers were produced.

Example 3 hPRL-G129R Homodimer Induces STAT 5 Phosphorylation

T-47D cells are grown in RPMI-1640 medium containing 10% charcoal stripped fetal bovine serum (CSFBS; growth medium). For each experiment, cells are passed into 6 well culture plates in growth medium until they are 90% confluent. On the day of the experiment, cells are placed in serum-free media for 1 hour and incubated with hPRL, wt-hPRL homodimer, or hPRL-G129R homodimer for 30 minutes. After treatment, T-47D cells are washed once with ice cold PBS and collected by gentle scraping in 1 ml ice-cold lysis buffer [20 mM Tris-Cl (pH 7.4), 100 mM NaCl, 2 mM EDTA, 1% NP-40, 1 mM PMSF, 10 ug/ml leupeptin]. The lysis mixture is then passed through a 22 gauge needle several times avoiding air bubbles and spun at maximum speed for 20 minutes. The supernatant is then transferred to a new microcentrifuge tube. 5 ug of STAT 5 monoclonal antibody [UBI, Lake Placid, N.Y.] is then added to 100 ul of cell lysate along with 400 ul of ddH20 and 500 ul of 2×IP buffer [1% Triton X-100, 150 mM NaCl, 10 mM Tris pH 7.4, 1 mM EDTA, 1 mM EGTA, 0.2 mM sodium vanadate, 0.2 mM PMSF, 0.5% NP-40] to each reaction. After overnight incubation at 4° C. and gentle rotation, 50 µl of prewashed (1×IP buffer) protein A agarose beads are added to each IP reaction and continue the incubation for another 2 hours at 4° C. At the end of the incubation, the agarose beads are washed 3× with 1×IP buffer and the protein eluted by resuspending the protein A agarose beads in 50 ul of 1×SDS PAGE loading buffer. Samples are then subjected to 4-12.5% SDS-PAGE immune blot analysis using HRP-conjugated anti-phosphotyrosine antibody (UBI, Lake Placid, N.Y.) and ECL reagent kit (Amersham, Ill.). Blots are then exposed to X-ray films and developed using standard procedures.

Figure 2:
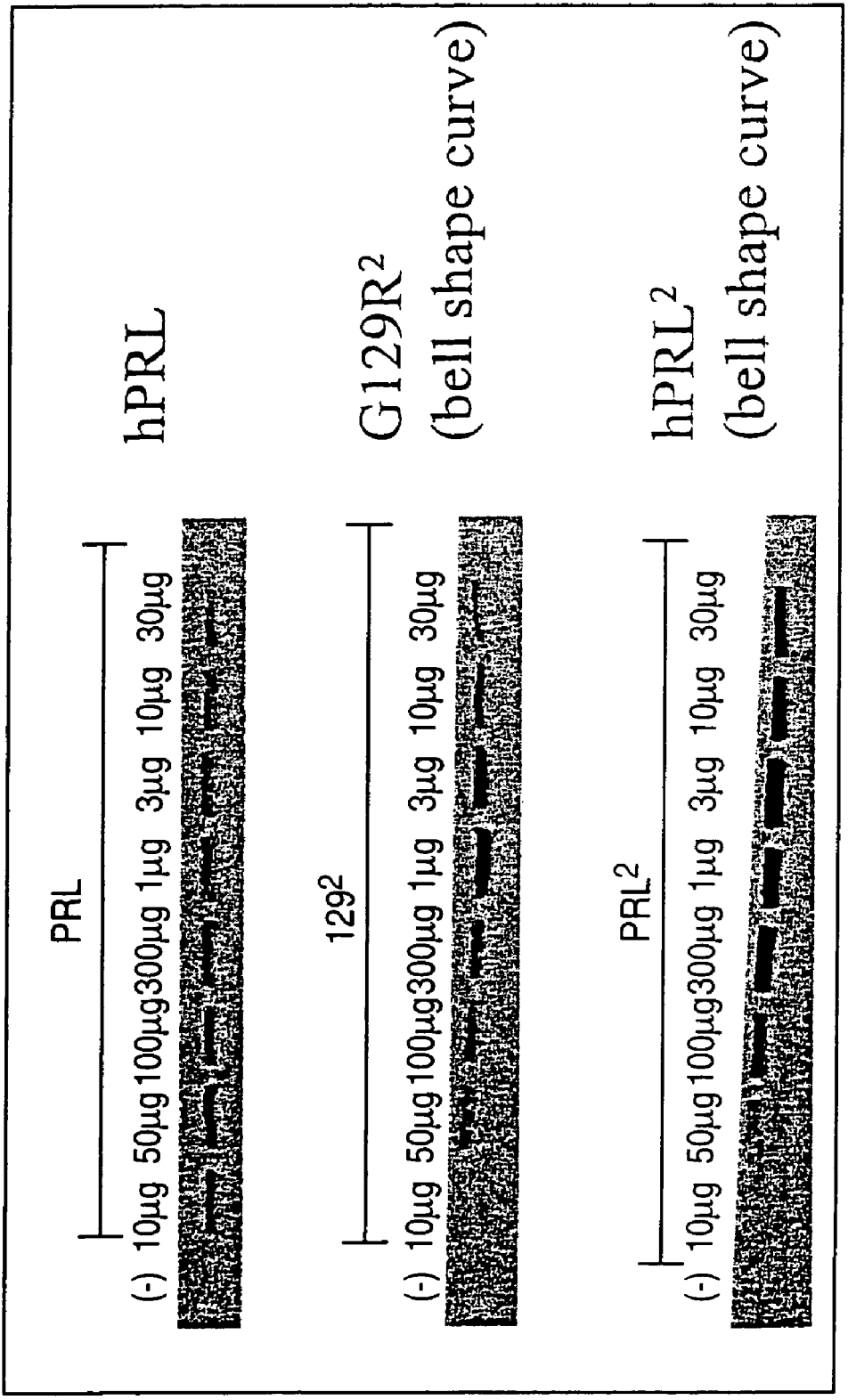
FIG. 2. Western blot analysis of STAT 5 phosphorylation in hPRL, hPRL-G129 homodimer and hPRL homodimer.
Figure 3:
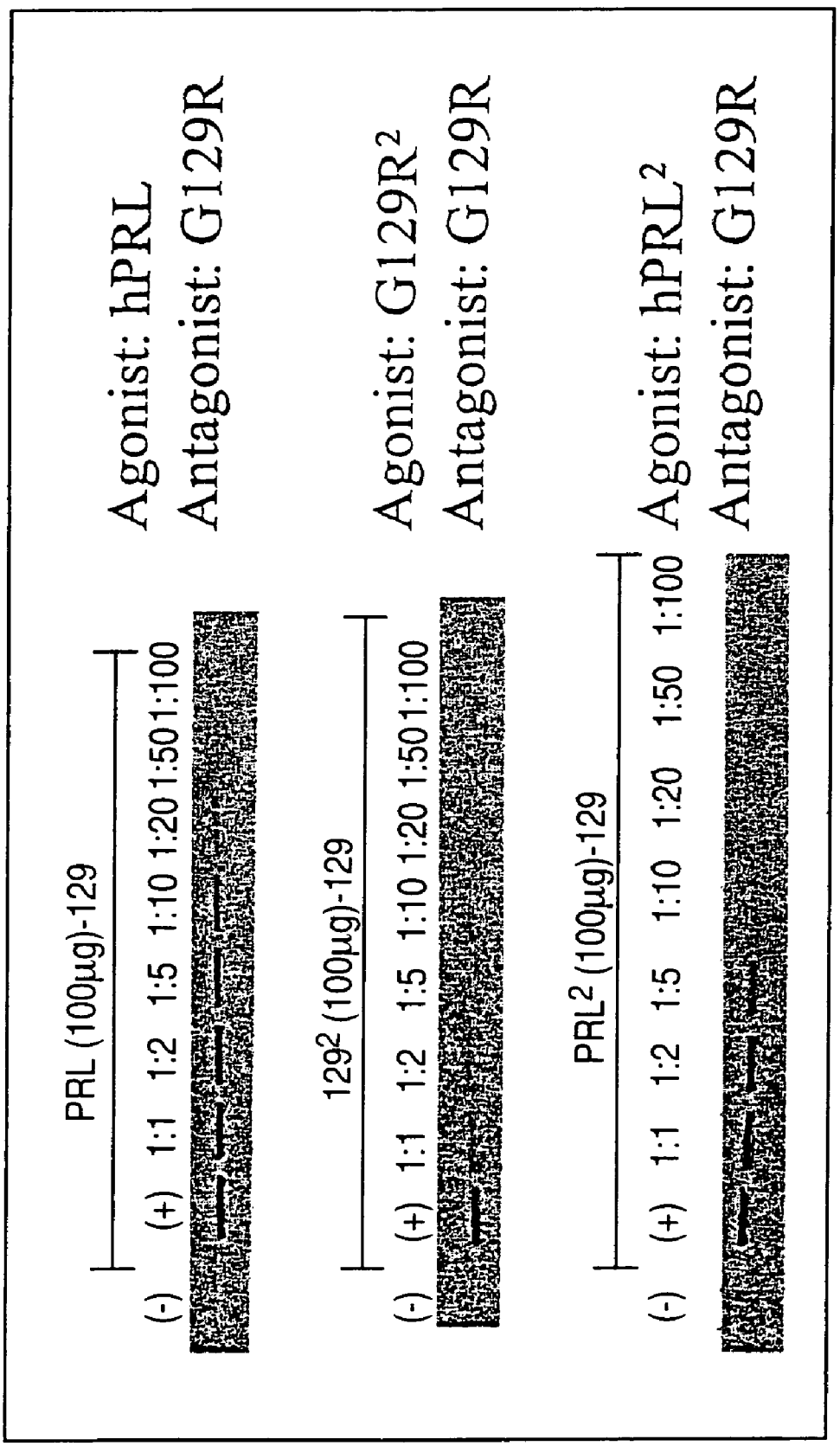
FIG. 3. Western blot analysis of STAT 5 phosphorylation in hPRL, hPRL-G129 homodimer and hPRL homodimer, indicating inhibition of prolactin cell signaling in the presence of a hPRL-G129R monomer.

As determined by STAT 5 phosphorylation, the hPRL-G129R homodimer acts as a prolactin agonist in human breast cancer cells. FIG. 2 indicates that STAT 5 phosphorylation is induced by hPRL-G129R and wt-hPRL homodimers. Additionally, the hPRL-G129R and wt-hPRL homodimers are able to induce STAT5 phosphorylation in a concentration-dependent manner at a dose range similar to that of the wild type hPRL monomer. Also, the bell-shaped phosphorylation signal for hPRL-G129R and wt-hPRL homodimers indicates that, as in the case of the hPRL monomer, self-antagonism is evident at high concentrations. See FIG. 2. Additionally, the activation of STAT5 phosphorylation by a hPRL-G129R homodimer or a wt-hPRL homodimer can be inhibited by a hPRL-G129R monomer. See FIG. 3.

These results suggest that as long as at least two binding sites are available in one molecule (site 1 plus site 2 in wild type hPRL or site 1 plus another site 1 in hPRL-G129R homo-dimer), the ligand acts as an agonist. The data also indicate that the overall size of the ligand is not a crucial factor (23 kd monomer or 46 kd dimer) to induce signal transduction.

What is claimed:

1. A protein comprising a receptor antagonist dimer, wherein said receptor antagonist dimer (i) is a receptor agonist and (ii) comprises a first monomer and a second monomer; wherein said first monomer is a wild-type human prolactin (hPRL) monomer that comprises an amino acid substitution at a position corresponding to 129 in hPRL, and said second monomer is selected from the group consisting of a wild-type human prolactin (hPRL) monomer that comprises an amino acid substitution at a position corresponding to 129 in hPRL, and a wild-type human growth hormone (hGH) monomer that comprises an amino acid substitution at a position corresponding to 120 in hGH.

2. The protein of claim 1, wherein said receptor antagonist dimer is a homodimer.

3. The protein of claim 1, wherein said first monomer comprises a Gly to Arg substitution at a position corresponding to 129 in hPRL.

4. A pharmaceutical composition comprising the protein of claim 1 and a pharmaceutically acceptable carrier.

5. The protein of claim 1, wherein said second monomer is a wild-type human growth hormone (hGH) monomer that comprises an amino acid substitution at a position corresponding to 120 in hGH.

6. The protein of claim 5, wherein said first monomer comprises a Gly to Arg substitution at a position corresponding to 129 in hPRL.

7. The protein of claim 1, wherein said amino acid substitution in said first monomer consists of a bulky side chain amino acid at position 129.

8. A protein comprising a receptor antagonist dimer, wherein said receptor antagonist dimer (i) is a receptor agonist and (ii) comprises a first monomer and a second monomer; wherein said first monomer is a wild-type human growth hormone (hGH) monomer that comprises an amino acid substitution at a position corresponding to 120 in hGH, and said second monomer is selected from the group consisting of a wild-type human prolactin (hPRL) monomer that comprises an amino acid substitution at a position corresponding to 129 in hPRL, and a wild-type human growth hormone (hGH) monomer that comprises an amino acid substitution at a position corresponding to 120 in hGH.

9. The protein of claim 8, wherein said receptor antagonist dimer is a homodimer.

10. The protein of claim 9, wherein said first monomer comprises a Gly to Arg substitution at a position corresponding to 120 in hGH.

11. The protein of claim 8, wherein said amino acid substitution in said first monomer consists of a bulky side chain amino acid at position 120.

\* \* \* \* \*

UNITED STATES PATENT AND TRADEMARK OFFICE
CERTIFICATE OF CORRECTION

| | | |
|---|---|---|
| PATENT NO. | : 7,632,809 B2 | Page 1 of 1 |
| APPLICATION NO. | : 10/419976 | |
| DATED | : December 15, 2009 | |
| INVENTOR(S) | : Wen Yuan Chen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 921 days.

Signed and Sealed this

Second Day of November, 2010

David J. Kappos
*Director of the United States Patent and Trademark Office*